United States Patent [19]

Renga et al.

[11] 4,387,237

[45] Jun. 7, 1983

[54] PROCESS FOR MAKING VICINAL EPOXIDES

[75] Inventors: James M. Renga, Midland; Gerald C. Kolb, Bay City, both of Mich.

[73] Assignee: The Dow Chemical Company, Midland, Mich.

[21] Appl. No.: 367,720

[22] Filed: Apr. 12, 1982

[51] Int. Cl.$^3$ ............................................ C07D 301/02
[52] U.S. Cl. .................................................... 549/518
[58] Field of Search ........................................ 549/518

[56] References Cited

U.S. PATENT DOCUMENTS

| 4,261,906 | 4/1981 | Renga et al. | 549/518 |
| 4,265,821 | 5/1981 | McEntire | 549/518 |
| 4,349,482 | 9/1982 | Renga et al. | 549/518 |

FOREIGN PATENT DOCUMENTS 53-46921 10/1978 Japan .

OTHER PUBLICATIONS

L. Shapiro et al., Zhur. Org. Khim., 5, 2, 207–212 (1969).
Yoshiharu Ishido et al., JCS, Perkin I, 521–530 (1977).
E. D. Bergmann et al., JCS, C, 899–900 (1966).

Primary Examiner—Norma S. Milestone
Attorney, Agent, or Firm—Douglas N. Deline

[57] ABSTRACT

Vicinal epoxides are prepared by decomposition of β-haloalkyl carbonates or bis(β-haloalkyl) carbonates in the presence of a complex of an alkali metal halide and a monomeric or polymeric chelating agent comprising an element of group V of the Periodic Table at a temperature from about 25° C. to about 250° C.

9 Claims, No Drawings

PROCESS FOR MAKING VICINAL EPOXIDES

BACKGROUND OF THE INVENTION

This invention relates to a new process for making vicinal epoxides.

Vicinal epoxides are valuable chemical intermediates and monomers useful in making epoxy adhesives and various heat- and solvent-resistant polymers. A well-known process for making vicinal epoxides from olefins involves the oxidation of the olefinic double bond with aqueous chlorine to form the chlorohydrin and reaction of the chlorohydrin with a base to make the epoxide. However, a major disadvantage of this process is the production of an equivalent of HCl from the aqueous oxychlorination step and another equivalent of inorganic chloride from the reaction of the base with the chlorohydrin intermediate. In the case of epichlorohydrin, the conventional preparation uses the same chemistry with the added initial step of chlorinating propylene to allyl chloride which produces an additional equivalent of HCl.

Ethylene oxide is prepared by oxidizing ethylene with molecular oxygen over a silver catalyst. However, this method is not applicable to other olefins because of low selectivity and the formation of by-products. Another method using oxygen involves oxidizing a hydrocarbon such as isobutane or isopropylbenzene with air to the corresponding tertiary hydroperoxide and then reacting the hydroperoxide with an olefin in the presence of a transition metal catalyst. A disadvantage of this process is the formation of co-product alcohol which must be sold or recycled.

Hydrogen peroxide and peroxy acids are other reagents which have been used to epoxidized olefins. Chemical and economic disadvantages of such methods have precluded their use on a large scale.

It is known that cyclic carbonates can be decomposed to form epoxides in the presence of various catalysts. Such a process particularly directed to the preparation of propylene oxide by decomposition of propylene carbonate in the presence of a sulfonium or phosphonium halide or any of certain metal salts is described in U.S. Pat. No. 4,069,234.

In U.S. Pat. No. 4,261,906, filed in the name of James M. Renga and another, it has been shown that vicinal epoxides of various kinds, not only the simple alkylene and cycloalkylene oxides, but also their aromatic and halogen-substituted derivatives, can be made in good yield by heating an unsymmetrical β-haloalkyl carbonate of the formula

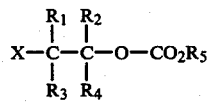

in the presence of a small but effective amount of a quaternary ammonium or phosphonium salt at a temperature of about 25° C.–250° C. The products of this decomposition are CO$_2$, the halide R$_5$X, and the epoxide of the formula

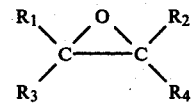

wherein X is Cl or Br, each of R$_1$, R$_2$, R$_3$ and R$_4$ is hydrogen, a hydrocarbon group, —CH$_2$X, or R$_1$ and R$_2$ together form an alkylene group of 3–6 carbon atoms, and R$_5$ is an alkyl group, preferably a lower alkyl group.

In Serial No. 238,188, filed Feb. 25, 1981, now U.S. Pat. No. 4,349,482 a continuation-in-part of the above-issued patent, bis(β-haloalkyl) carbonates are similarly catalytically pyrolyzed to prepare epoxides and alkylene dihalides.

It is known that certain alkali metal halides are effective catalysts for the decomposition of cyclic alkylene carbonates to the corresponding alkylene oxide or polyalkylene oxide. It is also known that certain alkali metal halide salts are effective catalysts in the reaction of phenolic or thiophenolic compounds with cyclic alkylene carbonates.

SUMMARY OF THE INVENTION

According to the present invention is provided a novel process for the formation of vicinal epoxide compounds of the formula

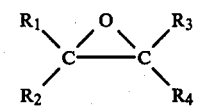

comprising contacting a carbonate reactant of the formula

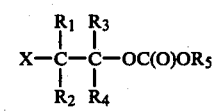

wherein

R$_1$, R$_2$, R$_3$ and R$_4$ are independently each occurrence hydrogen, hydrocarbyl, CH$_2$X or CH$_2$Y, and the adjacent pair R$_1$, R$_3$ may additionally form an alkylene group of 3–6 carbons;

R$_5$ is a C$_{1-10}$ alkyl group or

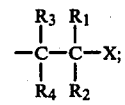

X is chloro or bromo; and

Y is alkoxy or aroxy, with a catalyst comprising a soluble complex of an alkali metal halide and a monomeric or polymeric chelating agent containing an element of group V of the Periodic Table at a temperature of about 25° C. to about 250° C.

DETAILED DESCRIPTION OF THE INVENTION

The term hydrocarbyl as used above to define the groups R$_1$–R$_4$ includes alkyl groups of one to about 20 carbon atoms, cycloalkyl and alkylcycloalkyl groups of 5–10 carbon atoms, and aryl groups of 6–10 carbon atoms.

Preferred carbonate reactants are those of the above supplied formula where $R_1$–$R_4$ each occurrence are hydrogen, methyl, $CH_2X$ or $CH_2Y$, where Y is $C_{1-4}$ alkoxy, phenoxy or bisphenoxy.

Most preferred carbonate reactants are those where one of $R_1$–$R_4$ is hydrogen or methyl and the remaining three are hydrogen. Examples of such most preferred carbonate reactants include: methyl 2-chloroethyl carbonate, bis-2-chloroethyl carbonate, methyl 2-bromoethyl carbonate, methyl 1-chloro-2-propyl carbonate, methyl 2-chloro-1-propyl carbonate, bis-1-chloro-2-propyl carbonate, 2-chloroethyl 1-chloro-2-propyl carbonate, etc., and mixtures thereof.

The unsymmetrical bis carbonates such as the latter mentioned 2-chloroethyl 1-chloro-2-propyl carbonate may be pyrolyzed according to the present invention to provide a mixture of alkylene oxides, e.g., ethylene oxide and propylene oxide for the above representative example.

The catalysts employed in the present invention are alkali metal halide salts that are rendered soluble in the carbonate ester by chelation with a monomeric or polymeric chelating agent containing a group V element, particularly nitrogen or phosphorus. Preferred chelating agents are compounds containing polar nitrogen or phosphorus functionality, e.g., amines, amides, phosphines, phosphoramides and phosphine oxides. Suitable examples include cyclic saturated or unsaturated nitrogen-containing compounds such as pyridines, pyrazines, triazines, tetrahydropyridines, pyrroles, imidazoles, pyrrolidines, imidazolines, oxazolidines, pyrrolidinones, etc.; aliphatic amine compounds such as ethylene diamine, tetraethylene pentamine, etc.; and phosphorus compounds such as trialkyl or triphenyl phosphines or phosphine oxides, etc.; and combinations of phosphorus- and nitrogen-containing compounds, e.g., hexaalkyl phosphoramides. Preferred chelating agents are N-methyl-2-pyrrolidinone, triphenylphosphine and hexamethylphosphoramide.

Without the presence of the above chelating agent, the alkali metal halide salts have been found to be insoluble in the carbonate reactant and ineffective to catalyze the reaction. Additional chelating agents such as cyclic polyethers or crown ethers and linear alkyl ethers of (poly)alkylene glycols have also proven ineffective or entirely inoperable according to the invention. Equally surprising is the discovery that the chelating agents alone do not possess any or much catalytic activity. The unique result of the invention appears to be due to the presence of both the alkali metal halide and the above named chelating agents.

The alkali metal halide salts for use according to the present invention are lithium, sodium or potassium fluorides, chlorides, bromides or iodides. Preferred is lithium chloride or sodium chloride.

The alkali metal halide salt is added in catalytically effective amounts. Generally, from about 0.1–10 mole percent of the alkali metal halide salt based on carbonate reactant is sufficient. The chelating agent is added in an amount sufficient to complex the alkali metal halide and may be present in excess over that required to form the complex. In particular, it may be of advantage to prepare a solution of alkali metal halide in excess chelate, for example, a dilute alkali metal halide solution in N-methyl-2-pyrrolidinone. To this solution the carbonate reactant may be added at the desired reaction temperature while simultaneously removing the reaction products, for example, by distillation. It is possible to limit the rate of addition so as to match the rate of product formation thereby establishing a steady state and continuous reaction process.

As can be seen from the preceding description, the invented process produces two useful kinds of product, mono- or dihaloalkane and epoxide, assuming $CO_2$ to be a waste product. The structure of the starting carbonate, therefore, is normally designed to produce not only the desired epoxide, but also a particular useful halogenated alkane which has a boiling point sufficiently different from the epoxide to facilitate easy and complete separation of these two products.

As noted previously, when an unsymmetrical bis($\beta$-haloalkyl)carbonate is employed, two different epoxides and two different alkylene dihalides are produced by the decomposition. The relative proportions of the products prepared depends upon the sizes of the two alkyl groups. Thus, when 2-chloroethyl 1-chloro-2-propyl carbonate is subjected to the conditions of the decomposition process, the principal epoxide and dihalide products are propylene oxide and ethylene dichloride with minor amounts of ethylene oxide and propylene dichloride being formed. Ordinarily, conventional distillation of the mixed products provides effective separation of the individual components as pure compounds.

When a symmetrical bis($\beta$-haloalkyl)carbonate is decomposed by this process, obviously only one epoxide and one alkylene dihalide are formed. For example, the decomposition of bis(2-chloroethyl)carbonate yields ethylene oxide and ethylene dichloride.

This process is ordinarily of most interest as a means of producing epoxides of higher molecular weight than ethylene oxide such as propylene oxide, epichlorohydrin, and alkyl or aryl glycidyl ethers. It has particular advantage in that the halide co-product is not a useless inorganic waste material but rather an economically desirable halogenated alkane.

The decomposition reaction takes place in the presence of the catalyst at some rate at any temperature from about room temperature to about 250° C., but for normally practical reaction times, the decomposition is preferably carried out at about 150° C.–250° C. Reaction times can range from 0.001 hour to about 10 hours depending on the structure of the carbonate, the temperature, and the nature and amount of the catalyst.

In a mode of the invention particularly adapted to continuous operation, the carbonate starting material can be passed at an appropriate flow rate through a vessel containing the chelated alkali metal halide salt catalyst maintained at a suitable temperature within the limits previously defined. The catalyst may be retained in the vessel by removing the products in the gas phase as they are formed.

In the preparation of higher boiling epoxides particularly, separation of the epoxide product may be facilitated by running the reaction under appropriately reduced pressure or by passing a stream of nitrogen or other inert gas through or over the reaction mixture.

The carbonate starting materials and particularly the bis($\beta$-haloalkyl)carbonates for this process can be prepared by several known procedures. The reaction of a chloroformate with an alcohol conventionally used for the preparation of carbonate esters is readily adapted to the preparation of these halogenated carbonates by using the appropriate halogenated alcohol and halogenated alkyl chloroformate reactants. Symmetrical bis(- haloalkyl)carbonates in particular can be made by the strong acid catalyzed transesterification reaction of a halogenated alcohol in excess with a dialkyl carbonate. Some of these carbonates can also be made by using an appropriate unsaturated alcohol in the transesterification reaction and then adding halogen or hydrogen halide to the unsaturated ester product. A method recently described in Japanese Pat. No. 46,921/78 whereby a cyclic carbonate such as ethylene carbonate or propylene carbonate is reacted at moderate temperature with an olefin and chlorine or bromine in equal molar amounts is another means of obtaining the halogenated alkyl carbonate starting materials of this invention. By using ethylene carbonate (which is made from ethylene oxide) and an olefin other than ethylene as reactants in the cited Japanese process to make the haloalkyl carbonate starting material of this invention, the present process becomes essentially a means for transferring the epoxide value of ethylene oxide to higher olefins using organic carbonates as intermediates.

SPECIFIC EMBODIMENTS

Having described the invention, the following examples are provided as further illustrative and are not to be construed as limiting.

EXAMPLE 1

2-Chloroethyl 1-chloro-2-propyl carbonate (10.05 g, 0.05 mole), lithium chloride (0.1 g, 0.002 mole) and N-methyl-2-pyrrolidinone (4.9 g, 0.05 mole) were charged to a 50-ml reaction flask equipped with a mechanical stirrer, condenser, receiver and cold trap. The receiver contained 50 ml of toluene and 2 ml tetrahydrofuran internal standard for gas chromatography analysis. The reaction flask was heated to 180° C.–185° C. in an oil bath with stirring for about 4 hours. The receiver was cooled to about 30° C. and used to collect volatile reaction products.

After 4 hours the reaction was discontinued. The reactor flask contained about 6.8 g of material that was found to contain about 0.53 g of 2-chloroethyl 1-chloro-2-propyl carbonate. This amounts to a 95 percent conversion. Analysis of the contents of the cold trap indicated a recovered product yield by weight of 67 percent propylene oxide and 8 percent ethylene oxide. Yields of chlorinated alkanes were 76 percent ethylene dichloride and 13 percent propylene dichloride.

EXAMPLE 2

A 10 percent solution of lithium chloride in N-methyl-2-pyrrolidinone (9.5 g) was charged to a 50-ml three-necked flask equipped with a mechanical stirrer, dropping funnel, condenser and receiver. The flask was placed in an oil bath and heated to 160° C.–165° C. 2-Chloroethyl 1-chloro-2-propyl carbonate (10.05 g) was added dropwise over a 1-hour period with stirring. The contents of the flask were heated with stirring an additional 2 hours. Analysis indicated 62 percent conversion of carbonate reactant. The recovered epoxide yields were 53 percent propylene oxide and 2 percent ethylene oxide. Yields of ethylene dichloride and propylene dichloride were 81 percent and 7 percent, respectively.

EXAMPLES 3–11

The reaction conditions of Example 1 were repeated employing LiCl (1.0 percent by weight based on carbonate), 2-chloroethyl 1-chloro-2-propyl carbonate (10.05 g, 0.05 mole) and the chelating agents more particularly defined in Table I.

TABLE I

| Example | Chelating Agent - moles | Temp. °C. | Reaction Time (hr) | % Conversion | % Selectivity PO[1] | EO[2] | EDC[3] | PDC[4] |
|---|---|---|---|---|---|---|---|---|
| 3 | pyridine - 0.0025 | 180 | 2 | 33 | 39 | — | 68 | 27 |
| 4 | tetraethylene pentamine - 0.0025 | 180 | 4 | 37 | 4 | — | 19 | 14 |
| 5 | N—methyl-2-pyrrolidinone - 0.050 | 180 | 2 | 76 | 53 | 6 | 73 | 9 |
| 6 | PVP K-30 ® (1.0 g)[5] | 180 | 2 | 21 | 35 | — | 47 | 5 |
| 7 | PVP K-90 ® (0.5 g)[5] | 180 | 4 | 17 | 24 | — | 42 | 14 |
| 8 | triphenyl phosphine oxide - 0.0025 | 180 | 4 | 28 | 49 | 4 | 66 | 10 |
| 9 | hexamethyl phosphoramide - 0.0055 | 180 | 2 | 74 | 58 | 7 | 78 | 10 |
| 10 | triphenyl phosphine - 0.0025 | 200 | 5 | 92 | 65 | 5 | 74 | 8 |
| 11 | TPM[6,7] | 200 | 4 | 26 | 14 | — | 45 | 45 |

[1]Propylene oxide
[2]Ethylene oxide
[3]Ethylene dichloride
[4]Propylene dichloride
[5]Polyvinylpyrrolidinone available commercialy from GAF Corporation
[6]Comparative example
[7]Monomethyl ether of tripropylene glycol

EXAMPLE 12

Comparative

The reaction conditions of Example 1 were again substantially repeated excepting that no alkali metal halide salt catalyst was employed. Accordingly, 50.0 mmoles of N-methyl-2-pyrrolidinone and 50.0 mmoles of 2-chloroethyl 1-chloro-2-propyl carbonate were combined and heated with stirring at 180° C. for about 4 hours. The conversion was 9 percent. Recovered yield of ethylene dichloride and propylene dichloride were 40 percent and 11 percent, respectively.

What is claimed is:

1. A process for making vicinal epoxide corresponding to the formula

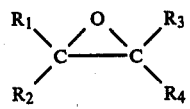

or a mixture thereof comprising contacting a carbonate reactant of the formula

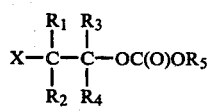

wherein $R_1$, $R_2$, $R_3$ and $R_4$ independently each occurrence are hydrogen, hydrocarbyl, $CH_2X$ or $CH_2Y$, and the adjacent pair $R_1$, $R_3$ may additionally form an alkylene group of 3–6 carbons;

$R_5$ is a $C_{1-10}$ alkyl group or

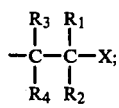

X is chloro or bromo; and
Y is alkoxy or aroxy, with a catalyst comprising a soluble complex of an alkali metal halide and a monomeric or polymeric chelating agent comprising an element of group V of the Periodic Table at a temperature of about 25° C. to about 250° C.

2. A process according to claim 1 wherein $R_1$–$R_4$ are each occurrence hydrogen, methyl, $CH_2X$ or $CH_2Y$ where Y is $C_{1-4}$ alkoxy, phenoxy or bisphenoxy.

3. A process according to claim 2 wherein one of $R_1$–$R_4$ is hydrogen or methyl and the remaining members of $R_1$–$R_4$ are hydrogen.

4. A process according to claim 3 wherein the carbonate reactant is 2-chloroethyl 1-chloro-2-propyl carbonate.

5. The process of claim 1 wherein the temperature is from about 150° C. to about 250° C.

6. The process of claim 1 wherein the alkali metal halide is a lithium, sodium or potassium fluoride, chloride, bromide or iodide.

7. The process of claim 6 wherein the alkali metal halide is lithium chloride or sodium chloride.

8. The process of claim 1 wherein the chelating agent is a polar nitrogen- or phosphorus-containing compound selected from the group consisting of amines, amides, phosphines, phosphoramides and phosphine oxides.

9. The process of claim 8 wherein the chelating agent is N-methyl-2-pyrrolidinone, hexamethylphosphoramide or triphenyl phosphine.

* * * * *